United States Patent
Hong et al.

(10) Patent No.: US 10,131,926 B2
(45) Date of Patent: Nov. 20, 2018

(54) TRANSAMINASE AND USES THEREOF

(71) Applicants: ASYMCHEM LABORATORIES (TIANJIN) CO., LTD, Tianjin (CN); ASYMCHEM LIFE SCIENCE (TIANJIN) CO., LTD, Tianjin (CN); TIANJIN ASYMCHEM PHARMACEUTICAL CO., LTD, Tianjin (CN); ASYMCHEM LABORATORIES (FUXIN) CO., LTD, Fuxin, Liaoning (CN); JILIN ASYMCHEM LABORATORIES CO., LTD, Dunhua, Jilin (CN)

(72) Inventors: Hao Hong, Tianjin (CN); Feng Gao, Tianjin (CN); Yanjun Li, Tianjin (CN); Yan Zhang, Tianjin (CN); Shaohe Li, Tianjin (CN)

(73) Assignees: ASYMCHEM LABORATORIES (TIANJIN) CO., LTD, Tianjin (CN); ASYMCHEM LIFE SCIENCE (TIANJIN) CO., LTD, Tianjin (CN); TIANJIN ASYMCHEM PHARMACEUTICAL CO., LTD, Tianjin (CN); ASYMCHEM LABORATORIES (FUXIN) CO., LTD, Fuxin, Liaoning (CN); JILIN ASYMCHEM LABORATORIES CO., LTD, Dunhua, Jilin (CN)

( * ) Notice: Subject to any disclaimer, the term of this patent is extended or adjusted under 35 U.S.C. 154(b) by 28 days.

(21) Appl. No.: 15/039,804

(22) PCT Filed: Oct. 31, 2014

(86) PCT No.: PCT/CN2014/090080
§ 371 (c)(1),
(2) Date: May 26, 2016

(87) PCT Pub. No.: WO2015/078267
PCT Pub. Date: Jun. 4, 2015

(65) Prior Publication Data
US 2017/0073713 A1    Mar. 16, 2017

(30) Foreign Application Priority Data
Nov. 26, 2013    (CN) .......................... 2013 1 0611503

(51) Int. Cl.
*C12N 9/10* (2006.01)
*C12N 15/70* (2006.01)
(Continued)

(52) U.S. Cl.
CPC .............. *C12P 13/001* (2013.01); *C12N 1/20* (2013.01); *C12N 9/1096* (2013.01); *C12N 15/70* (2013.01); *C12P 17/12* (2013.01); *C12Y 206/01* (2013.01)

(58) Field of Classification Search
CPC ........................... C12N 9/1096; C12Y 206/01
See application file for complete search history.

(56) References Cited

U.S. PATENT DOCUMENTS

2012/0156706 A1*  6/2012  Hoehne ................ C12N 9/1096
                                                            435/16

FOREIGN PATENT DOCUMENTS

| CN | 101512005 A | 8/2009 |
| CN | 102482650 A | 5/2012 |

(Continued)

OTHER PUBLICATIONS

UniProt Accession No. E0MQP7_9RHOB, published Oct. 3, 2012.*
(Continued)

*Primary Examiner* — Richard C Ekstrom
(74) *Attorney, Agent, or Firm* — Pearl Cohen Zedek Latzer Baratz LLP

(57) ABSTRACT

A transaminase and a use thereof are provided. The transaminase has the amino acid sequences as shown in SEQ ID NO: 2 or 4, or has at least 80% identity to the amino acid sequences as shown in SEQ ID NO: 2 or 4, or has amino acid sequences which are obtained by the substitution, deletion or addition of one or more amino acids and have an the activity of an omega-transaminase with high stereoselective R-configuration catalytic activity, wherein the high stereoselective refers to the content of one of the stereoisomers being at least about 1.1 times that of the other.

14 Claims, 3 Drawing Sheets

Specification includes a Sequence Listing.

(51) Int. Cl.
C12N 1/20 (2006.01)
C12P 13/00 (2006.01)
C12P 17/12 (2006.01)

(56) References Cited

FOREIGN PATENT DOCUMENTS

| | | |
|---|---|---|
| EP | 1818411 A1 | 8/2007 |
| JP | 07 289252 A | 11/1995 |
| JP | 10 075787 A | 9/1996 |
| JP | 2002 539791 A | 11/2002 |
| JP | 2004 033161 A | 2/2004 |
| JP | 2009 526531 A | 7/2009 |
| JP | 2010 502202 A | 1/2010 |
| JP | 2011 514141 A | 5/2011 |
| JP | 2012 511930 A | 5/2012 |
| JP | 2013 503610 A | 2/2013 |
| WO | WO 2010/081053 A2 | 1/2009 |
| WO | WO 200988949 A1 | 7/2009 |
| WO | WO-2012007548 A1 * | 1/2012 ............ C12P 13/001 |
| WO | WO 2012/124639 A1 | 9/2012 |

OTHER PUBLICATIONS

Karim Engelmark Cassimjee et al. "Chromobacterium violaceum ω-transaminase variant Trp60Cys shows increased specificity for (S)-1-phenylethylamine and 4'-substituted acetophenones, and follows Swain-Lupton parameterization", Org. Biomol. Chem., 2012, vol. 28, No. 10, pp. 5466-5470, Jul. 28, 2012.

Jong-Shik Shin et al. "Asymmetric Synthesis of Chiral Amines With ω-Transaminase", Laboratory of Molecular Biotechnology and Biomaterials, Biotechnology, and Bioengineering, vol. 65, No. 2, pp. 206-211, Oct. 20, 1999.

Jong-Shik Shin et al. "Comparison of the ω-Transaminases from Different Microorganisms and Application to Production of Chiral Amines", Bioscience, Biotechnology, and Biochemistry, vol. 65, No. 8, pp. 1782-1788, Aug. 31, 2001.

Jia et al. "Progress in ω-transaminase in chiral amine synthesis", Modern Chemical Industry, vol. 32, No. 3, pp. 16-22, Mar. 31, 2012.

International Search Report of PCT Application No. PCT/CN2014/090080, dated Feb. 10, 2015.

Database GenBank, aminotransferase, class IV [Hyphomonas neptunium ATCC 15444]. Nov. 21, 2011. URL: http://www.ncbi.nlm.nih.gov/protein/114737414?sat=18&satkey=1856240.

Shin, Jong-Shik et al. "Comparison of the ω-Transaminases from Different Microorganisms and Application to Production of Chiral Amines." *Bioscience, Biotechnology, and Biochemistry*, vol. 65, No. 8, 2001, pp. 1782-1788.

Shin, Jong-Shik, et al. "Asymmetric Synthesis of Chiral Amines with ω-Transaminase." *Biotechnology & Bioengineering*, vol. 65, No. 2, 1999, pp. 206-211.

* cited by examiner

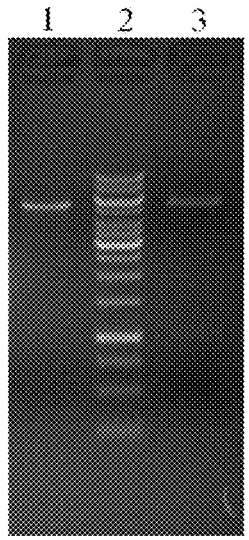

Fig. 3

```
taAT.seq       MASMDKVFAGYAARQAILESTETDNPFAKGIAWVEGELVPLAEARIPLLDQGFMHSDLTY    60
AH-TACM33.seq  MASMDKVFAGYAARQAILESTETDNPFAKGIAWVEGELVPLAEARIPLLDQGFMHSDLTY    60
taHN.seq       MLTFQKVLIGFQTRAD..ARAERIDAEADGIAWIENEFVPIGKARIPLLDQGFHSDLTY     58
Consensus         m  kv g    r     e t   fa giaw e e vp   arip ldqgf hsdlty taAT.seq       DVPSVWDGRFFRLDDHITRLEASCTKLRLRLPEDQVKQILVEMVAKSGIRDAFVELIV    120
AH-TACM33.seq  DVPSVWDGRFFRLDDHITRLEASCTKLRLRLPEDQVKQILVEMVAKSGIRDAFVELIV    120
taHN.seq       DVPAVWNGRIFRLDDELDRLEVSCAKMRLPLEIARPELRRLVMELVSRSGLRDAYVEIIV   118
Consensus      dvp vw gr frlddh  rle sc k rl lp  r        e v  sg rda ve iv taAT.seq       TRGLKGVRGTRPEDIVNNLYMFVQPYVWVMEPDMCRVGGSAVVARTVRRVPPGAIDPTVK   180
AH-TACM33.seq  TRGLKGVRGTRPEDIVNNLYMFVQPYVWVMEPDMCRVGGSAVVARTVRRVPPGAIDPTVK   180
taHN.seq       TRGLKFLRGAQAEDIIPNLYLMAVPYVWILPLEYQNHGAPAVVTRTVRRTPPGALDPTIK   178
Consensus      trglk   rg  edi  nly   pyvw       q g  avv rtvrr ppga dpt k taAT.seq       NLQWGDLVRGMFEAADRGATYPFLTDGDAHLTEGSGFNIVLKDCVRYTPDRGVLQGVTR   240
AH-TACM33.seq  NLQWGDLVRGMFEAADRGATYPFLTDGDAHLTEGAGYNIVLVRNGELHTPRRGVLEGITR   240
taHN.seq       NLQWGDLVRGLMEEGGRDSFFPILPDGDGNATEGAGYNIVLVRNGELHTPRRGVLEGITR   238
Consensus      nlqwgdlvrg  ea  dr     p l dgd    teg g nivlv  g l tp rgvl g tr taAT.seq       KSVINAAEAFGIEVRVEFVPVELAYPCDEIFMCTAGGIMPITTLDGMPVNGGQIGPITK    300
AH-TACM33.seq  RTVLEIAAARGLKTHVTEIPIQALYECDELFMCSTAGGIMPLVLLDGNIVGDCTVGPVTR   300
taHN.seq       RTVLEIAAARGLKTHVTEIPIQALYECDELFMCSTAGGIMPLVLLDGNIVGDCTVGPVTR   298
Consensus        v   aa g  v   p    y cde fmc taggimp   ldg  v gp t taAT.seq       KIWDGYWAMFYDAAYSFEIDYNERNL                                    326
AH-TACM33.seq  MIWEAYWDLRDDPQLSEPVTMAP..L                                    324
taHN.seq       MIWEAYWDLRDDPQLSEPVTMAP..L                                    322
Consensus       iw  yw  h d   s   y   l
```

Fig. 4

SEQUENCE LISTING

```
<160> NUMBER OF SEQ ID NOS: 25

<210> SEQ ID NO 1
<211> LENGTH: 975
<212> TYPE: DNA
<213> ORGANISM: Artificial Sequence
<220> FEATURE:
<223> OTHER INFORMATION: recombinant transaminase gene AH-TACM32

<400> SEQUENCE: 1
atggcgtcta tggacaaagt ttttgcaggt tacgcggccc gtcaagcgat cctggaatct      60
actgagacta ccaacccgtt cgcgaaaggt atcgcgtggg tagaaggtga actggttccg     120
ctggcggaag cacgcatccc gctgctggat cagggcttca tgcattccga cctgacgtat     180
gacgtgccgt ctgtgtggga tggccgcttc ttccgtctgg atgatcacat cactcgtctg     240
gaagcatcct gcactaaact gcgtctgcgc ctgcctctgc cgcgtgatca ggtgaaacag     300
atcctggttg aaatggttgc gaaatccggc attcgcgacg cgtttgtcga actgattgtc     360
acccgcggtc tgaagggtgt gcgtggcacc cgtccggaag acattgtaaa caacctgtac     420
atgttcgtgc agccgtacgt ctgggttatg gaaccggaca tgcagcgtgt tggcggcagc     480
gcagttgtag cccgtaccgt tcgtcgtact ccgccgggcg cactggatcc gactattaaa     540
```

```
aacctgcagt ggggcgatct ggttcgcggt ctgatggaag caggcgaccg tgattctttc      600
tttcctattc tgccggatgg cgacggtaac gcgacggaag gcgcaggcta caatatcgta      660
ctggtgcgta acggcgagct gcataccccg cgtcgtggcg ttctggaagg tattacccgt      720
cgtacggtgc tggagattgc agctgctcgc ggcctgaaaa ctcacgtcac cgaaatccca      780
atccaggccc tgtatgaatg cgacgaactg tttatgtgca gcaccgcggg cggtatcatg      840
ccactggtgc tgctggatgg caacattgta ggtgacggca ccgttggtcc ggtcacccgc      900
atgatttggg aagcgtactg ggacctgcac gacgacccgc agctgtctga accggtaacc      960
tatgcaccgc tcgag                                                       975
```

<210> SEQ ID NO 2
<211> LENGTH: 325
<212> TYPE: PRT
<213> ORGANISM: Artificial Sequence
<220> FEATURE:
<223> OTHER INFORMATION: recombinant transaminase gene AH-TACM32

<400> SEQUENCE: 2

```
Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Thr Pro Pro Gly Ala Leu Asp
                165                 170                 175

Pro Thr Ile Lys Asn Leu Gln Trp Gly Asp Leu Val Arg Gly Leu Met
            180                 185                 190

Glu Ala Gly Asp Arg Asp Ser Phe Phe Pro Ile Leu Pro Asp Gly Asp
        195                 200                 205

Gly Asn Ala Thr Glu Gly Ala Gly Tyr Asn Ile Val Leu Val Arg Asn
    210                 215                 220

Gly Glu Leu His Thr Pro Arg Arg Gly Val Leu Glu Gly Ile Thr Arg
225                 230                 235                 240

Arg Thr Val Leu Glu Ile Ala Ala Ala Arg Gly Leu Lys Thr His Val
                245                 250                 255

Thr Glu Ile Pro Ile Gln Ala Leu Tyr Glu Cys Asp Glu Leu Phe Met
            260                 265                 270

Cys Ser Thr Ala Gly Gly Ile Met Pro Leu Val Leu Leu Asp Gly Asn
```

```
            275                 280                 285
Ile Val Gly Asp Gly Thr Val Gly Pro Val Thr Arg Met Ile Trp Glu
    290                 295                 300

Ala Tyr Trp Asp Leu His Asp Asp Pro Gln Leu Ser Glu Pro Val Thr
305                 310                 315                 320

Tyr Ala Pro Leu Glu
            325
```

<210> SEQ ID NO 3
<211> LENGTH: 975
<212> TYPE: DNA
<213> ORGANISM: Artificial Sequence
<220> FEATURE:
<223> OTHER INFORMATION: recombinant transaminase gene AH-TACM33

<400> SEQUENCE: 3

```
atggcgtcta tggacaaagt ttttgcaggt tacgcggccc gtcaagcgat cctggaatct    60
actgagacta ccaacccgtt cgcgaaaggt atcgcgtggg tagaaggtga actggttccg   120
ctggcggaag cacgcatccc gctgctggat cagggcttca tgcattccga cctgacgtat   180
gacgtgccgt ctgtgtggga tggccgcttc ttccgtctgg atgatacat cactcgtctg    240
gaagcatcct gcactaaact gcgtctgcgc ctgcctctgc cgcgtgatca ggtgaaacag   300
atcctggttg aaatggttgc gaaatccggc attcgcgacg cgtttgtcga actgattgtc   360
acccgcggtc tgaagggtgt gcgtggcacc cgtccggaag acattgtaaa caacctgtac   420
atgttcgtgc agccgtacgt ctgggttatg aaccggaca tgcagcgtgt tggcggcagc    480
gcagttgtag cccgtaccgt tcgtcgtgtt ccgcctggcg caatcgaccc aactgttaaa   540
aatctgcagt gggcgatct ggtacgcggt atgtttgaag ctgccgatcg tggtgctact    600
tatccgttcc tgacggatgg tgacgctcac ctgaccgagg gcgcaggcta caatatcgta   660
ctggtgcgta acggcgagct gcataccccg cgtcgtggcg ttctggaagg tattacccgt   720
cgtacggtgc tggagattgc agctgctcgc ggcctgaaaa ctcacgtcac cgaaatccca   780
atccaggccc tgtatgaatg cgacgaactg tttatgtgca gcaccgcggg cggtatcatg   840
ccactggtgc tgctggatgg caacattgta ggtgacggca ccgttggtcc ggtcacccgc   900
atgatttggg aagcgtactg ggacctgcac gacgacccgc agctgtctga accggtaacc   960
tatgcaccgc tcgag                                                   975
```

<210> SEQ ID NO 4
<211> LENGTH: 325
<212> TYPE: PRT
<213> ORGANISM: Artificial Sequence
<220> FEATURE:
<223> OTHER INFORMATION: recombinant transaminase AH-TACM33

<400> SEQUENCE: 4

```
Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80
```

Glu Ala Ser Cys Thr Lys Leu Arg Leu Arg Leu Pro Leu Pro Arg Asp
                    85                  90                  95

Gln Val Lys Gln Ile Leu Val Glu Met Val Ala Lys Ser Gly Ile Arg
                100                 105                 110

Asp Ala Phe Val Glu Leu Ile Val Thr Arg Gly Leu Lys Gly Val Arg
            115                 120                 125

Gly Thr Arg Pro Glu Asp Ile Val Asn Asn Leu Tyr Met Phe Val Gln
130                 135                 140

Pro Tyr Val Trp Val Met Glu Pro Asp Met Gln Arg Val Gly Gly Ser
145                 150                 155                 160

Ala Val Val Ala Arg Thr Val Arg Val Pro Pro Gly Ala Ile Asp
                165                 170                 175

Pro Thr Val Lys Asn Leu Gln Trp Gly Asp Leu Val Arg Gly Met Phe
            180                 185                 190

Glu Ala Ala Asp Arg Gly Ala Thr Tyr Pro Phe Leu Thr Asp Gly Asp
                195                 200                 205

Ala His Leu Thr Glu Gly Ala Gly Tyr Asn Ile Val Leu Val Arg Asn
            210                 215                 220

Gly Glu Leu His Thr Pro Arg Arg Gly Val Leu Glu Gly Ile Thr Arg
225                 230                 235                 240

Arg Thr Val Leu Glu Ile Ala Ala Ala Arg Gly Leu Lys Thr His Val
                245                 250                 255

Thr Glu Ile Pro Ile Gln Ala Leu Tyr Glu Cys Asp Glu Leu Phe Met
            260                 265                 270

Cys Ser Thr Ala Gly Gly Ile Met Pro Leu Val Leu Leu Asp Gly Asn
                275                 280                 285

Ile Val Gly Asp Gly Thr Val Gly Pro Val Thr Arg Met Ile Trp Glu
290                 295                 300

Ala Tyr Trp Asp Leu His Asp Asp Pro Gln Leu Ser Glu Pro Val Thr
305                 310                 315                 320

Tyr Ala Pro Leu Glu
                325

<210> SEQ ID NO 5
<211> LENGTH: 981
<212> TYPE: DNA
<213> ORGANISM: Aspergillus terreus

<400> SEQUENCE: 5
atggcaagca tggataaagt ttttgcaggt tatgcagcac gtcaggcaat tctggaaagc      60
accgaaacca ccaatccgtt tgcaaaaggt attgcatggg ttgaaggtga actggttccg     120
ctggcagaag cacgtattcc gctgctggat cagggtttta tgcatagcga tctgacctat     180
gatgttccga gcgtttggga tggtcgtttt tttcgtctgg atgatcatat taccgtctg     240 gaagcaagct gtaccaaact gcgtctgcgt ctgccgctgc ctcgtgatca ggttaaacaa     300
attctggttg aaatggttgc caaaagcggt attcgtgatg catttgttga actgattgtt     360
acccgtggtc tgaaaggtgt tcgtggcacc cgtccggaag atattgttaa taatctgtat     420
atgtttgtgc agccgtatgt ttgggttatg gaaccggata tgcagcgtgt tggtggtagc     480
gcagttgttg cacgtaccgt tcgtcgtgtt ccgccgggtg caattgatcc gaccgttaaa     540
aatctgcagt ggggtgatct ggttcgtggt atgtttgaag cagcagatcg tggtgcaacc     600
tatccgtttc tgaccgatgg tgatgcacat ctgaccgaag gtgcgggctt taacattgtt     660

```
ctggttaaag atggcgtgct gtatacaccg atcgtggtg ttctgcaggg tgttacccgt      720
aaaagcgtta ttaatgcagc agaagccttt ggtattgaag ttcgtgttga atttgttccg      780
gttgaactgg catatcgctg tgatgaaatc tttatgtgta ccaccgcagg cggtattatg      840
ccgattacca ccctggatgg tatgccggtt aatggtggtc agattggtcc gattaccaaa      900
aaaatctggg atggttattg ggccatgcat tatgatgcag catatagctt tgaaattgat      960
tataatgaac gcaatctcga g                                                981

<210> SEQ ID NO 6
<211> LENGTH: 969
<212> TYPE: DNA
<213> ORGANISM: Neptune silk Aeromonas

<400> SEQUENCE: 6
atgctgacct ttcagaaagt tctgaccggt tttcagaccc gtgcagatgc acgtgcagaa       60
cgtaccgatg catttgcaga tggtattgca tggattgaaa atgaatttgt gccgattggc      120
aaagcacgta ttccgattct ggatcagggt tttctgcata cgatctgac ctatgatgtt      180 ccggcagttt ggaatggtcg tattttttcgt ctggatgatc atctggatcg tctggaagtt      240
agctgtgcaa aaatgcgtct gccgctgccg attcacgtc cggaactgcg tcgtctggtt      300
atggaactgg ttagccgtag cggtctgcgt gatgcctatg ttgaaattat tgttacccgt      360
ggcctgaaat ttctgcgtgg tgcacaggca gaagatatta ttccgaatct gtatctgatg      420
gccgttccgt atgtttggat tctgccgctg aatatcaga atcatggtgc accggcagtt      480
gttacccgta ccgttcgtcg taccgccgcg ggtgcactgg atccgaccat caaaaatctg      540
cagtggggtg atctggttcg tggtctgatg gaagccggtg atcgtgatag cttttttccg      600
attctgccgg atggtgatgg taatgcaacc gaaggtgcag gctataacat tgttctggtt      660
cgtaatggcg aactgcatac accgcgtcgt ggtgttctgg aaggtattac ccgtcgtacc      720
gttctggaaa ttcagcagc acgtggcctg aaaacacatg ttaccgaaat tccgattcag      780
gcactgtatg aatgtgatga actgtttatg tgtagcaccg caggcggtat tatgccgctg      840
gttctgctgg atggtaatat tgttggtgat ggcaccgttg gtccggttac ccgtatgatt      900
tgggaagcat attgggatct gcatgatgat ccgcagctga gcgaaccggt tacctatgca      960
ccgctcgag                                                              969

<210> SEQ ID NO 7
<211> LENGTH: 33
<212> TYPE: DNA
<213> ORGANISM: Artificial Sequence
<220> FEATURE:
<223> OTHER INFORMATION: primer of a transaminase gene

<400> SEQUENCE: 7
ccgctcgagg ttacgctcgt tgtagtcaat ttc                                    33

<210> SEQ ID NO 8
<211> LENGTH: 29
<212> TYPE: DNA
<213> ORGANISM: Artificial Sequence
<220> FEATURE:
<223> OTHER INFORMATION: primer of a transaminase gene

<400> SEQUENCE: 8
ggaattccat atggcgtcta tggacaaag                                         29
```

```
<210> SEQ ID NO 9
<211> LENGTH: 30
<212> TYPE: DNA
<213> ORGANISM: Artificial Sequence
<220> FEATURE:
<223> OTHER INFORMATION: primer for a transaminase gene of Neptune silk
      Aeromonas

<400> SEQUENCE: 9
ccgctcgagc ggtgcatagg ttaccggttc                                    30

<210> SEQ ID NO 10
<211> LENGTH: 36
<212> TYPE: DNA
<213> ORGANISM: Artificial Sequence
<220> FEATURE:
<223> OTHER INFORMATION: primer for a transaminase gene of Neptune silk
      Aeromonas

<400> SEQUENCE: 10
ggaattccat atgctgacct tccaaaaagt actgac                             36

<210> SEQ ID NO 11
<211> LENGTH: 27
<212> TYPE: DNA
<213> ORGANISM: Artificial Sequence
<220> FEATURE:
<223> OTHER INFORMATION: antisense primer for a fragment of transaminase
      gene

<400> SEQUENCE: 11
gaacttcaga ccgcgggtga caatcag                                       27

<210> SEQ ID NO 12
<211> LENGTH: 23
<212> TYPE: DNA
<213> ORGANISM: Artificial Sequence
<220> FEATURE:
<223> OTHER INFORMATION: sense primer for a fragment of transaminase
      gene

<400> SEQUENCE: 12
cacccgcggt ctgaagttcc tgc                                           23

<210> SEQ ID NO 13
<211> LENGTH: 24
<212> TYPE: DNA
<213> ORGANISM: Artificial Sequence
<220> FEATURE:
<223> OTHER INFORMATION: antisense primer for a fragment of transaminase
      gene

<400> SEQUENCE: 13
cggcggaaca cgacgaacgg tacg                                          24

<210> SEQ ID NO 14
<211> LENGTH: 24
<212> TYPE: DNA
<213> ORGANISM: Artificial Sequence
<220> FEATURE:
<223> OTHER INFORMATION: sense primer for a fragment of transaminase
      gene

<400> SEQUENCE: 14
ttcgtcgtac tccgccgggc gcac                                          24

<210> SEQ ID NO 15
```

```
<211> LENGTH: 25
<212> TYPE: DNA
<213> ORGANISM: Artificial Sequence
<220> FEATURE:
<223> OTHER INFORMATION: antisense primer for a fragment of transaminase
      gene

<400> SEQUENCE: 15
tagcctgcgc cctcggtcag gtgag                                              25

<210> SEQ ID NO 16
<211> LENGTH: 25
<212> TYPE: DNA
<213> ORGANISM: Artificial Sequence
<220> FEATURE:
<223> OTHER INFORMATION: sense primer for a fragment of transaminase
      gene

<400> SEQUENCE: 16
gaccgagggc gcaggctaca atatc                                              25

<210> SEQ ID NO 17
<211> LENGTH: 27
<212> TYPE: DNA
<213> ORGANISM: Artificial Sequence
<220> FEATURE:
<223> OTHER INFORMATION: antisense primer for a fragment of transaminase
      gene

<400> SEQUENCE: 17
cccttcagac cacgcgtaac gatgatc                                            27

<210> SEQ ID NO 18
<211> LENGTH: 27
<212> TYPE: DNA
<213> ORGANISM: Artificial Sequence
<220> FEATURE:
<223> OTHER INFORMATION: sense primer for a fragment of transaminase
      gene

<400> SEQUENCE: 18
ttacgcgtgg tctgaagggt gtgcgtg                                            27

<210> SEQ ID NO 19
<211> LENGTH: 28
<212> TYPE: DNA
<213> ORGANISM: Artificial Sequence
<220> FEATURE:
<223> OTHER INFORMATION: antisense primer for a fragment of transaminase
      gene

<400> SEQUENCE: 19
ccaggcggag tacgacgtac agtacgag                                           28

<210> SEQ ID NO 20
<211> LENGTH: 26
<212> TYPE: DNA
<213> ORGANISM: Artificial Sequence
<220> FEATURE:
<223> OTHER INFORMATION: sense primer for a fragment of transaminase
      gene

<400> SEQUENCE: 20
tacgtcgtgt tccgcctggc gcaatc                                             26

<210> SEQ ID NO 21
<211> LENGTH: 24
```

```
<212> TYPE: DNA
<213> ORGANISM: Artificial Sequence
<220> FEATURE:
<223> OTHER INFORMATION: antisense primer for a fragment of transaminase
      gene

<400> SEQUENCE: 21
gccgctgcct tccgtcgcgt tacc                                            24

<210> SEQ ID NO 22
<211> LENGTH: 25
<212> TYPE: DNA
<213> ORGANISM: Artificial Sequence
<220> FEATURE:
<223> OTHER INFORMATION: sense primer for a fragment of transaminase
      gene

<400> SEQUENCE: 22
gacggaaggc agcggcttca acatc                                           25

<210> SEQ ID NO 23
<211> LENGTH: 327
<212> TYPE: PRT
<213> ORGANISM: Aspergillus terreus

<400> SEQUENCE: 23
```

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Leu Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Arg Val Pro Pro Gly Ala Ile Asp
                165                 170                 175

Pro Thr Val Lys Asn Leu Gln Trp Gly Asp Leu Val Arg Gly Met Phe
            180                 185                 190

Glu Ala Ala Asp Arg Gly Ala Thr Tyr Pro Phe Leu Thr Asp Gly Asp
        195                 200                 205

Ala His Leu Thr Glu Gly Ser Gly Phe Asn Ile Val Leu Val Lys Asp
    210                 215                 220

Gly Val Leu Tyr Thr Pro Asp Arg Gly Val Leu Gln Gly Val Thr Arg
225                 230                 235                 240

Lys Ser Val Ile Asn Ala Ala Glu Ala Phe Gly Ile Glu Val Arg Val
                245                 250                 255

```
Glu Phe Val Pro Val Glu Leu Ala Tyr Arg Cys Asp Glu Ile Phe Met
            260                 265                 270

Cys Thr Thr Ala Gly Gly Ile Met Pro Ile Thr Thr Leu Asp Gly Met
        275                 280                 285

Pro Val Asn Gly Gly Gln Ile Gly Pro Ile Thr Lys Lys Ile Trp Asp
    290                 295                 300

Gly Tyr Trp Ala Met His Tyr Asp Ala Ala Tyr Ser Phe Glu Ile Asp
305                 310                 315                 320

Tyr Asn Glu Arg Asn Leu Glu
                325

<210> SEQ ID NO 24
<211> LENGTH: 323
<212> TYPE: PRT
<213> ORGANISM: Neptune silk Aeromonas

<400> SEQUENCE: 24

Met Leu Thr Phe Gln Lys Val Leu Thr Gly Phe Gln Thr Arg Ala Asp
1               5                   10                  15

Ala Arg Ala Glu Arg Thr Asp Ala Phe Ala Asp Gly Ile Ala Trp Ile
            20                  25                  30

Glu Asn Glu Phe Val Pro Ile Gly Lys Ala Arg Ile Pro Ile Leu Asp
        35                  40                  45

Gln Gly Phe Leu His Ser Asp Leu Thr Tyr Asp Val Pro Ala Val Trp
    50                  55                  60

Asn Gly Arg Ile Phe Arg Leu Asp Asp His Leu Asp Arg Leu Glu Val
65                  70                  75                  80

Ser Cys Ala Lys Met Arg Leu Pro Leu Pro Ile Ala Arg Pro Glu Leu
                85                  90                  95

Arg Arg Leu Val Met Glu Leu Val Ser Arg Ser Gly Leu Arg Asp Ala
            100                 105                 110

Tyr Val Glu Ile Ile Val Thr Arg Gly Leu Lys Phe Leu Arg Gly Ala
        115                 120                 125

Gln Ala Glu Asp Ile Ile Pro Asn Leu Tyr Leu Met Ala Val Pro Tyr
    130                 135                 140

Val Trp Ile Leu Pro Leu Glu Tyr Gln Asn His Gly Ala Pro Ala Val
145                 150                 155                 160

Val Thr Arg Thr Val Arg Arg Thr Pro Pro Gly Ala Leu Asp Pro Thr
                165                 170                 175

Ile Lys Asn Leu Gln Trp Gly Asp Leu Val Arg Gly Leu Met Glu Ala
            180                 185                 190

Gly Asp Arg Asp Ser Phe Phe Pro Ile Leu Pro Asp Gly Asp Gly Asn
        195                 200                 205

Ala Thr Glu Gly Ala Gly Tyr Asn Ile Val Leu Val Arg Asn Gly Glu
    210                 215                 220

Leu His Thr Pro Arg Arg Gly Val Leu Glu Gly Ile Thr Arg Arg Thr
225                 230                 235                 240

Val Leu Glu Ile Ala Ala Ala Arg Gly Leu Lys Thr His Val Thr Glu
                245                 250                 255

Ile Pro Ile Gln Ala Leu Tyr Glu Cys Asp Glu Leu Phe Met Cys Ser
            260                 265                 270

Thr Ala Gly Gly Ile Met Pro Leu Val Leu Asp Gly Asn Ile Val
        275                 280                 285

Gly Asp Gly Thr Val Gly Pro Val Thr Arg Met Ile Trp Glu Ala Tyr
    290                 295                 300
```

Trp Asp Leu His Asp Asp Pro Gln Leu Ser Glu Pro Val Thr Tyr Ala
305                 310                 315                 320

Pro Leu Glu

<210> SEQ ID NO 25
<211> LENGTH: 325
<212> TYPE: PRT
<213> ORGANISM: Artificial Sequence
<220> FEATURE:
<223> OTHER INFORMATION: Leu to Ile substitution at 38th of AH-TACM32

<400> SEQUENCE: 25

Met Ala Ser Met Asp Lys Val Phe Ala Gly Tyr Ala Ala Arg Gln Ala
1               5                   10                  15

Ile Leu Glu Ser Thr Glu Thr Thr Asn Pro Phe Ala Lys Gly Ile Ala
            20                  25                  30

Trp Val Glu Gly Glu Ile Val Pro Leu Ala Glu Ala Arg Ile Pro Leu
        35                  40                  45

Leu Asp Gln Gly Phe Met His Ser Asp Leu Thr Tyr Asp Val Pro Ser
    50                  55                  60

Val Trp Asp Gly Arg Phe Phe Arg Leu Asp Asp His Ile Thr Arg Leu
65                  70                  75                  80

Glu Ala Ser Cys Thr Lys Leu Arg Leu Arg Leu Pro Leu Pro Arg Asp
                85                  90                  95

Gln Val Lys Gln Ile Leu Val Glu Met Val Ala Lys Ser Gly Ile Arg
            100                 105                 110

Asp Ala Phe Val Glu Leu Ile Val Thr Arg Gly Leu Lys Gly Val Arg
        115                 120                 125

Gly Thr Arg Pro Glu Asp Ile Val Asn Asn Leu Tyr Met Phe Val Gln
    130                 135                 140

Pro Tyr Val Trp Val Met Glu Pro Asp Met Gln Arg Val Gly Gly Ser
145                 150                 155                 160

Ala Val Val Ala Arg Thr Val Arg Arg Thr Pro Pro Gly Ala Leu Asp
                165                 170                 175

Pro Thr Ile Lys Asn Leu Gln Trp Gly Asp Leu Val Arg Gly Leu Met
            180                 185                 190

Glu Ala Gly Asp Arg Asp Ser Phe Phe Pro Ile Leu Pro Asp Gly Asp
        195                 200                 205

Gly Asn Ala Thr Glu Gly Ala Gly Tyr Asn Ile Val Leu Val Arg Asn
    210                 215                 220

Gly Glu Leu His Thr Pro Arg Arg Gly Val Leu Glu Gly Ile Thr Arg
225                 230                 235                 240

Arg Thr Val Leu Glu Ile Ala Ala Ala Arg Gly Leu Lys Thr His Val
                245                 250                 255

Thr Glu Ile Pro Ile Gln Ala Leu Tyr Glu Cys Asp Glu Leu Phe Met
            260                 265                 270

Cys Ser Thr Ala Gly Gly Ile Met Pro Leu Val Leu Leu Asp Gly Asn
        275                 280                 285

Ile Val Gly Asp Gly Thr Val Gly Pro Val Thr Arg Met Ile Trp Glu
    290                 295                 300

Ala Tyr Trp Asp Leu His Asp Asp Pro Gln Leu Ser Glu Pro Val Thr
305                 310                 315                 320

Tyr Ala Pro Leu Glu
                325

TRANSAMINASE AND USES THEREOF

CROSS-REFERENCE TO RELATED APPLICATIONS

This application is a National Phase Application of PCT International Application No. PCT/CN2014/090080, International Filing Date Oct. 31, 2014, claiming priority of Chinese Patent Application No. 201310611503.8, filed Nov. 26, 2013, which is hereby incorporated by reference.

FIELD OF THE INVENTION

The present invention relates to the field of synthesis of chiral compounds, and particularly to a transaminase and uses thereof.

BACKGROUND OF THE INVENTION

Chiral amines are ubiquitous in nature. They are common structural units in many important bioactive molecules, both synthetic and natural in origin. Chiral amines are a common structural motif in many drugs. Many chiral amines are also important chiral auxiliaries and chiral selectors. Therefore, the preparation of chiral amines is of significant economic importance.

At present, chiral amines are mainly prepared by means of chemical reduction, and amines with optical activity are prepared by using prochiral ketones. Catalyzed by Pd/C and quinine, a prochiral ketone reacts with formic acid and an ammonia or an organic primary amine to generate a chiral amine. Other researchers obtained a chiral amine through asymmetric amination and reduction of a prochiral ketone using a ruthenium complex as a catalyst (Renat Kadyrov et al. Highly Enantioselective Hydrogen-Transfer Reductive Amination: Catalytic Asymmetric Synthesis of Primary Amines. Angewandte Chemie International Edition. 2003, 42 (44), Page 5472 to Page 5474). The metal catalyst in such a reaction is a very critical factor and demands strict requirements on the metal catalyst. Also, it is necessary to carry out the reaction at high temperature and there are high requirements on operation devices. Additionally, the metal catalyst is expensive and an environmental pollutant (Ohkuma T et al. Trans-RuH (eta1-BH4) (binap) (1,2-diamine): a catalyst for asymmetric hydrogenation of simple ketones under base-free conditions. Journal of the American Chemical Society. 2002, 124(23), Page 6508 to Page 6509).

An aminotransferase, also known as a transaminase, may catalyze an exchange process between amino and carbonyl groups of alpha-amino acids. An omega-transaminase is a transaminase capable of catalysing a transamination reaction using substrates other than alpha-amino acid. Omega-transaminase may effectively produce a chiral amine through stereoselective transamination using a variety of ketones as raw materials. The omega-transaminase has attracted more and more attention by researchers because of its use of relatively cheap substrates and its ability to produce highly pure products. It is expected that the potential of omega-transaminase can be fully applied toward the industrial production of chiral amines. However, there is still a need for further research and invention of this class of enzyme.

There is a demand for an omega-transaminase with high catalytic activity and stereoselectivity toward the R-configuration so that demand for chiral amine can be satisfied.

SUMMARY OF THE INVENTION

The present invention aims to provide a new transaminase and the uses thereof to satisfy demands of industrial production of chiral amines.

A transaminase or a modified compound, functional equivalent, functional fragment or variant thereof is provided according to an aspect of the present invention so as to achieve the purpose above. The amino sequence of the transaminase comprises a sequence selected from one of the following sequences: a) an amino acid sequence as shown in SEQ ID NO: 2 or 4; b) an amino acid sequence with at least 80% identity to the amino acid sequence as shown in SEQ ID NO: 2 or 4 and having the activity of an omega-transaminase with high stereoselective R-configuration catalytic activity, wherein the amino acid sequence is not the amino acid sequence encoded by a nucleotide sequence as shown in SEQ ID NO: 5 or 6; c) a protein which is derived from SEQ ID NO: 2 or 4 by subjecting the amino acid sequence as shown in SEQ ID NO: 2 or 4 to substitution, deletion or addition one or more amino acids, and having the activity of an omega-transaminase with high stereoselective R-configuration catalytic activity, wherein the amino acid sequence is not the amino acid sequence encoded by the nucleotide sequence as shown in SEQ ID NO: 5 or 6, wherein the high stereoselectivity refers to the content of one of the stereoisomers being at least about 1.1 times that of the other.

Further, the amino acid sequence of the transaminase is an amino acid sequence acquired by substituting leucine at the $38^{th}$ site of the amino acid sequence as shown in SEQ ID NO: 2 by isoleucine.

A nucleotide is provided according to another aspect of the present invention. The nucleotide encodes the transaminase or the modified compound, functional equivalent, functional fragment or variant thereof.

Further, the sequence of the nucleotide comprises a sequence selected from one of the following sequences: a) a nucleotide sequence as shown in SEQ ID NO: 1 or 3; b) a nucleotide sequence with at least 80% identity to the nucleotide sequence as shown in SEQ ID NO: 1 or 3 and encoding an omega-transaminase with high stereoselective R-configuration catalytic activity, wherein the nucleotide sequence is not the nucleotide sequence as shown in SEQ ID NO: 5 or 6; c) a nucleotide sequence capable of hybridizing with the nucleotide sequence as shown in SEQ ID NO: 1 or 3 under highly stringent conditions and encoding an omega-transaminase with high stereoselective R-configuration catalytic activity, wherein the nucleotide sequence is not the nucleotide sequence as shown in SEQ ID NO: 5 or 6, wherein the high stereoselective refers to the content of one of the stereoisomers being at least about 1.1 times that of the other.

A recombinant vector is provided according to another aspect of the present invention. The nucleotide is effectively connected in the recombinant vector.

Further, the recombinant vector is pET22b-CM32 or pET22b-CM33.

A host cell is provided according to another aspect of the present invention. The foregoing recombinant vector is transformed or transfected into the host cell.

A method for synthesizing a chiral amine is provided according to another aspect of the present invention. The method includes the following steps: making a ketone compound, the transaminase or the modified compound, functional equivalent, functional fragment or variant thereof, pyridoxal phosphate, and an amino donor to react in a reaction system so as to obtain the chiral amine of R configuration.

Further, the ketone compound is

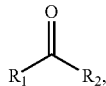

wherein $R_1$ and $R_2$ are independently $C_1$ to $C_8$ alkyl, $C_5$ to $C_{10}$ cycloalkyl, $C_5$ to $C_{10}$ aryl or $C_5$ to $C_{10}$ heteroaryl; or $R_1$ and $R_2$ form a $C_5$ to $C_{10}$ heterocyclic radical, a $C_5$ to $C_{10}$ carbocyclic radical or $C_5$ to $C_{10}$ heteroaryl with a carbon on a carbonyl group; heteroatoms in the $C_5$ to $C_{10}$ heterocyclic radical and $C_5$ to $C_{10}$ heteroaryl are independently selected from at least one of nitrogen, oxygen and sulfur; the aryl in the $C_5$ to $C_{10}$ aryl, the heteroaryl in the $C_5$ to $C_{10}$ heteroaryl, the carbocyclic radical in the $C_5$ to $C_{10}$ carbocyclic radical or the heterocyclic radical in the $C_5$ to $C_{10}$ heterocyclic radical is independently unsubstituted or is substituted by at least one radical of halogen, alkoxy or alkyl; preferably, the ketone compound

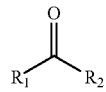

is selected from

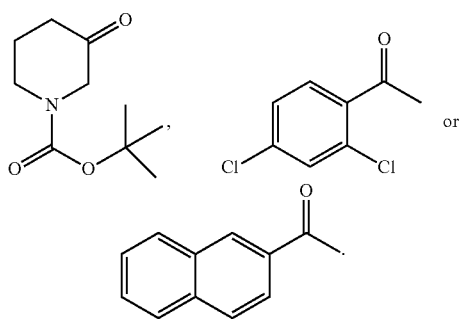

Further, the reaction system further includes a dissolution promoter, and the dissolution promoter is dimethyl sulfoxide or polyethylene glycol, and the polyethylene glycol is preferably PEG-400.

Further, the C1 to C8 alkyl is C1 to C8 linear alkyl, the C5 to C10 heteroaryl is a pyridine group, the alkoxy is C1 to C6 alkoxy, the heterocyclic radical in the C5 to C10 heterocyclic radical is piperidine, a substituent on the aryl in the C5 to C10 aryl, the heteroaryl in the C5 to C10 heteroaryl, the carbocyclic radical in the C5 to C10 carbocyclic radical or the heterocyclic radical in the C5 to C10 heterocyclic radical is independently C1 to C6 linear alkyl or C1 to C6 alkoxy, and the amino donor is isopropylamine or D-alanine.

By means of the technical solutions of the present invention, an omega-transaminase of R-configuration having a high stereoselectivity, or a modified compound, functional equivalent, functional fragment or variant thereof may be used for highly efficient synthesis of a chiral amine of R-configuration with a relatively high chiral purity, and is therefore suitable for industrial production of chiral amines.

BRIEF DESCRIPTION OF THE DRAWINGS

The accompanying drawings of the specification, which constitute a part of the application, are used for providing further understanding to the present invention. The exemplary embodiments of the present invention and illustration thereof are used for explaining the present invention, instead of constituting improper limitation to the present invention. In the accompanying drawings:

FIG. 3 shows an identification result of enzyme digestion in the first embodiment of the present invention;

FIG. 4 shows a sequencing result of a mutant gene having been subjected to a Polymerase Chain Reaction (PCR) in the first embodiment of the present invention;

DETAILED DESCRIPTION OF THE INVENTION

Figure 1:
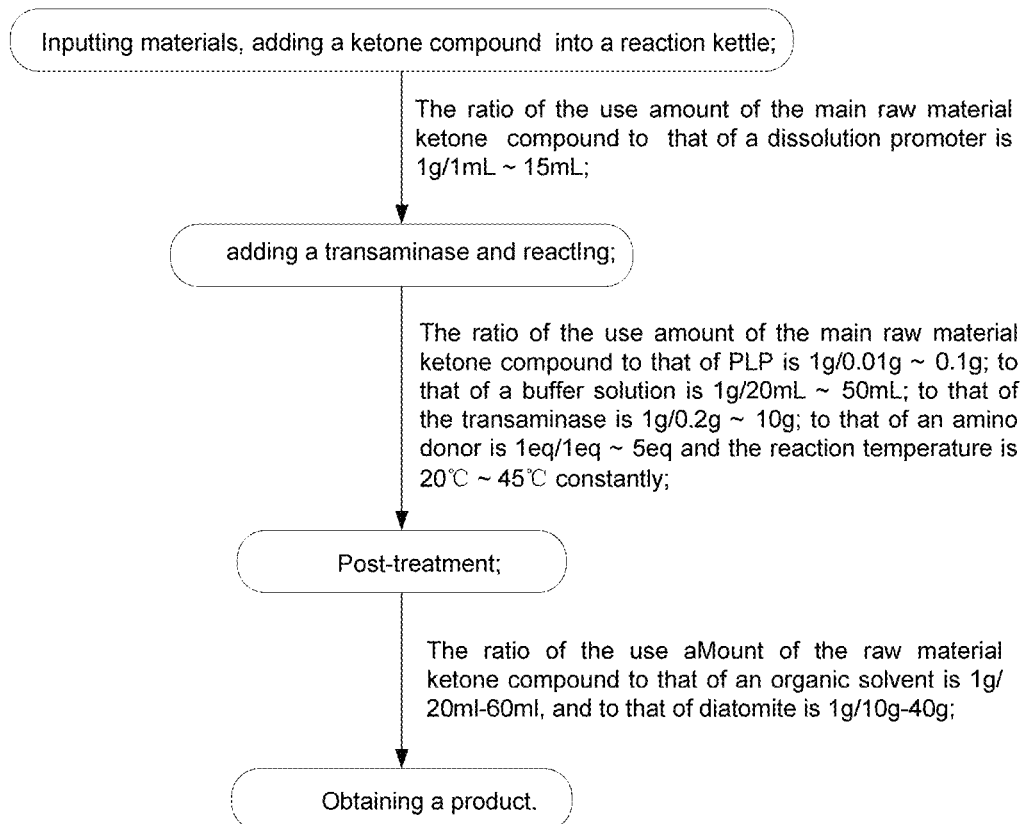
FIG. 1 shows a flowchart of a chemical reaction of a use of a transaminase derived from *Aspergillus terreus* and *Hyphomonas neptunium* in synthesis of a chiral amine according to an embodiment of the present invention.
Figure 2:
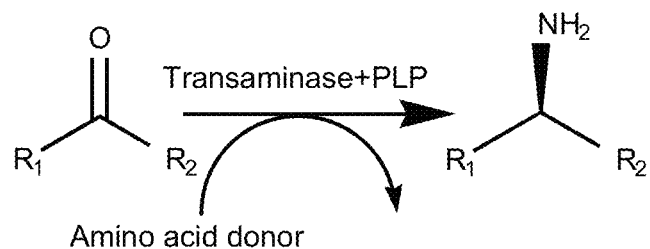
FIG. 2 is an equation of a chemical reaction of a use of a transaminase derived from *Aspergillus terreus* and *Hyphomonas neptunium* in synthesis of a chiral amine according to an embodiment of the present invention.

It needs to be noted that the embodiments in the application and the characteristics in the embodiments may be combined with each other if there is no conflict. The present invention will be expounded hereinafter with reference to the accompanying drawings and in conjunction with the embodiments.

Definition

The term "optional/random" or "optionally/randomly" means that an event or a situation in description thereinafter may happen or may not happen. The description includes that the event or the situation happens or does not happen. For example, "optionally substituted alkyl" refers to "unsubstituted alkyl" (alkyl that has not been substituted by a substituent) or "substituted alkyl" (alkyl that has been substituted by a substituent), as defined hereinafter.

The C1 to Cn used herein includes C1 to C2, C1 to C3, . . . C1 to Cn. For example, the "C1 to C4" radical means that the part has 1 to 4 carbon atoms, that is, the radical includes 1 carbon atom, 2 carbon atoms, 3 carbon atoms or 4 carbon atoms.

The term "alkyl" used separately or in combination herein refers to optionally substituted linear chain or optionally substituted branched chain aliphatic hydrocarbons. The "alkyl" herein may preferably have 1 to about 20 carbon atoms, e.g. 1 to about 10 carbon atoms, 1 to about 8 carbon atoms, 1 to about 6 carbon atoms, 1 to about 4 carbon atoms or 1 to about 3 carbon atoms. The term "alkoxy" used separately or in combination herein refers to an alkyl ether group (O-alkyl). Nonrestrictive embodiments of alkoxy include: methoxy, ethoxy, n-propoxy, isopropoxy, n-butoxy, isobutoxy, sec-butoxy, tert-butoxy and so on.

The term "halogenated" or "halogen substituted" used separately or in combination herein means that one or more hydrogen atoms in an optionally substituted radical (such as alkyl, alkenyl and alkynyl) are replaced by atoms of fluorine, chlorine, bromine, iodine, or a combination thereof.

The term "aromatic base/aryl" used separately or in combination herein refers to optionally substituted aromatic hydrocarbyl having 6 to about 20 cyclization carbon atoms, e.g. 6 to about 12 or 6 to about 10 cyclization carbon atoms, and may be a condensed aromatic ring or a non-condensed aromatic ring.

The term "heteroaryl" used separately or in combination herein refers to optionally substituted univalent heteroaryl including 5 to about 20, e.g. 5 to about 12, or 5 to about 10 framework cyclization atoms, wherein one or more (e.g. 1 to 4, 1 to 3, or 1 to 2) cyclization atoms are heteroatoms, and the heteroatoms are independently selected from heteroatoms in oxygen, nitrogen, sulfur, phosphorus, silicon, selenium and tin, but are not limited thereby. A ring of the radical does not include two adjacent O or S atoms. Heteroaryl includes monocyclic heteroaryl or polycyclic heteroaryl (such as dicyclic heteroaryl, tricyclic heteroaryl and so on).

The term "heterocycle" or "heterocyclic radical" used separately or in combination herein refers to a non-aromatic heterocycle, including heterocycloalkyl, and heterocycloalkenyl, wherein one or more (1 to 4, 1 to 3 or 1 to 2) cyclization atoms are heteroatoms, such as oxygen atoms, nitrogen atoms, or sulfur atoms. A heterocyclic radical may include a monoheterocyclic radical (a heterocyclic radical having one ring), or a polyheterocyclic radical (e.g. a diheterocyclic radical (a heterocyclic radical having two rings), a triheterocyclic radical and so on).

The term "carbocyclic radical" used separately or in combination herein refers to a non-aromatic carbon ring, including cycloalkyl and cycloalkenyl. The cycloalkyl may be monocyclic cycloalkyl or polycyclic cycloalkyl (e.g. having 2, 3, or 4 rings, such as dicyclic cycloalkyl), and may be a spiral ring or a bridge ring. A carbocyclic radical may have 3 to 20 carbon atoms, such as 3 to about 15 cyclization carbon atoms, 3 to about 10 cyclization carbon atoms or 3 to 6 cyclization carbon atoms, and may have 0, 1, 2 or 3 double bonds and/or 0, 1 or 2 triple bonds, e.g. cycloalkyl having 3 to 8 or 3 to 6 cyclization carbon atoms.

"Halogen" refers to fluorine, chlorine, bromine, and iodine, preferably fluorine, chlorine and bromine. Cyano refers to "—CN", hydroxyl refers to "—OH", mercapto refers to "—SH" and amino refers to "—$NH_2$".

The term "substituted" means that one or more hydrogen groups on a specific atom are substituted by a designated radical. If the normal valence of the designated atom is in, but is not beyond an existing condition, the substitution results in a stable compound.

As mentioned in the background, an omega-transaminase in the prior art still fails to satisfy demands for preparation of a compound of a chiral amine, and the present invention provides an omega-transaminase of R-configuration or a modified compound, functional equivalent, functional fragment or variant thereof in order to improve the situation above. The amino sequence of the omega-transaminase of R-configuration include a sequence selected from the following sequences: a) an amino acid sequence as shown in SEQ ID NO: 2 or 4; b) an amino acid sequence with at least 80% identity to the amino acid sequences as shown in SEQ ID NO: 2 or 4 and having the activity of an omega-transaminase with high stereoselective R-configuration catalytic activity, wherein the amino acid sequence is not the amino acid sequences encoded by a nucleotide sequences as shown in SEQ ID NO: 5 or 6; c) a protein which is derived from SEQ ID NO: 2 or 4 by subjecting the amino acid sequence as shown in SEQ ID NO: 2 or 4 to substitution, deletion or addition one or more amino acids, and having the activity of an omega-transaminase with high stereoselective R-configuration catalytic activity, wherein the amino acid sequence is not the amino acid sequence encoded by the nucleotide sequence as shown in SEQ ID NO: 2 or 4, wherein the high stereoselectivity refers to the content of one of the stereoisomers being at least about 1.1 times that of the other.

The omega-transaminase of R-configuration of the present invention refers to an omega-transaminase having a high R-configuration stereoselectivity. In an embodiment, the transaminase of the present invention refers to the transaminase as shown in SEQ ID NO: 2 or 4. The transaminase is a new transaminase obtained by subjecting transaminase genes taAT and taHN derived from *Aspergillus terreus* and *Hyphomonas neptunium* to mutation and modification by means of a molecular biological technique.

The amino acid sequence with at least 80% identity to the amino acid sequence as shown in SEQ ID NO: 2 or 4 and having the activity of an omega-transaminase with high stereoselective R-configuration catalytic activity refers to a sequence, which has at least 85%, 90%, 95%, 96%, 97%, 98%, 99%, 99.5% or 99.7% identity, for example, to the amino acid sequence as shown in SEQ ID NO: 2, but is not the amino acid sequence as shown in SEQ ID NO: 5. While keeping amino acids playing keyroles in the catalytic activity of the transaminase among the amino acid sequence as shown in SEQ ID NO: 2 or 4 unchanged, those skilled in the art may change remaining amino acid sequences of inactive sites, so that the amino acid sequence of an obtained transaminase has at least more than 80% identity to the amino acid sequence as shown in SEQ ID NO: 2, and the transaminase obtained in this way has the same transaminase activity as that of a transaminase having amino acid sequence as shown in SEQ ID NO: 2 or 4.

Similarly, one or more amino acids may be substituted, deleted or added to the amino acids in the amino acid sequence as shown in SEQ ID NO: 2 or 4 while keeping the amino acids playing key roles in the catalytic activity of the transaminase among the amino acid sequences shown in SEQ ID NO: 2 or 4 unchanged, thus a protein derived from SEQ ID NO: 2 or 4 can keep the high stereoselectivity of the transaminase as shown in SEQ ID NO: 2 or 4, wherein there may be one or more substituted, deleted or added bases, e.g. 1, 2, 3, 4, 5, 10, 20, 30 or 50 amino acids, e.g. substitution of conserved amino acids, wherein the amino acid sequence is not the amino acid sequence as shown in SEQ ID NO: 5. "Replacement of conserved amino acids" refers to combinations such as Gly, Ala; Val, Ile, Leu; Asp, Glu; Asn, Gln; Ser, Thr; Lys, Arg; and Phe and Tyr.

The stereoselectivity means that when two stereoisomers A and B are generated in a reaction, the yield of A is more than that of B, and the high stereoselectivity refers to the content of one of the stereoisomers being at least about 1.1 times that of the other, e.g. at least about 1.2 times, at least about 1.3 time, at least about 1.4 times, at least about 1.5 times, at least about 2 times, at least about 3 times, at least about 4 times, at least about 5 times, at least about 10 times, at least about 15 times, at least about 20 times, at least about 30 times, at least about 40 times, at least about 50 times, at least about 70 times, at least about 90 times, at least about 100 times or higher.

In the present invention, the modified compound of the omega-transaminase of R-configuration may be a chemical modified compound, such as a product of acylation, alkylation, or Polyethylene Glycolation (PEGylation), as long as these modified compounds maintain the activity of the omega-transaminase with the high stereoselective R-configuration catalytic activity. The functional equivalent refers to other peptide fragments that can realize the activity of the omega-transaminase of R-configuration. The functional fragment refers to a protein fragment that keeps the activity of the omega-transaminase with the high stereoselective R-configuration catalytic activity. The variant refers to a polypeptide derived from a parental protein by changing one or more amino acids at one or more (several) sites, i.e. by substation, insertion and/or deletion.

In a preferred embodiment of the present invention, the amino acid sequence of the transaminase is an amino acid sequence acquired by substituting leucine at the $38^{th}$ site of the amino acid sequence as shown in SEQ ID NO: 2 by isoleucine. Such replacement between amino acids having similar properties enables the transaminase having the amino acid sequence replaced maintains the activity of the transaminase having the amino acid sequence as shown in SEQ ID NO: 2 and high stereoselectivity.

The transaminase obtained by the present invention, which is an omega-transaminase with high stereoselective R-configuration catalytic activity, can be used for highly efficient synthesis of a chiral amine of R-configuration with a relatively high chiral purity, and is therefore suitable for industrial production of chiral amines. The present invention selects a splicing object and a splicing site in an optimized manner, so that a new transaminase variant obtained by transformation does not affect folding of proteins while maintaining the transaminase activity, having relatively high transaminase activity and high stereoselectivity.

A nucleotide is provided in another typical embodiment. The nucleotide encodes the omega-transaminase of R-configuration or the modified compound, functional equivalent, functional fragment or variant thereof, and an encoding rule of the nucleotide of the omega-transaminase of R-configuration or the modified compound, functional equivalent, functional fragment or variant thereof accords with a conventional codon usage table.

In a more preferred embodiment of the present invention, the sequences of the nucleotide include a sequence selected from one of the following sequences: a) a nucleotide sequence as shown in SEQ ID NO: 1 or 3; b) a nucleotide sequence which has at least 80% identity to the nucleotide sequence as shown in SEQ ID NO: 1 or 3 and encodes an omega-transaminase with high stereoselective R-configuration catalytic activity, wherein the nucleotide sequence is not the nucleotide sequence as shown in SEQ ID NO: 5 or 6; c) a nucleotide sequence with capable of hybridizing with the nucleotide sequence as shown in SEQ ID NO: 1 or 3 under highly stringent conditions and encoding an omega-transaminase having high stereoselective R-configuration catalytic activity, wherein the nucleotide sequence is not the nucleotide sequence as shown in SEQ ID NO: 4 or 6, wherein the high stereoselectivity refers to the content of one of the stereoisomers being at least about 1.1 times that of the other.

The nucleotide sequence with at least 80% identity to the nucleotide sequence as shown in SEQ ID NO.:1 or 3 and encoding the omega-transaminase having the high stereoselective R-configuration catalytic activity, having at least 85%, 90%, 95%, 96%, 97%, 98%, 99%, 99.5%, 99.7%, 99.8% or 99.9% identity, for example, is not the nucleotide sequence as shown in SEQ ID NO: 5 or 6. While keeping nucleotides playing key roles in the catalytic activity of the transaminase unchanged based on the nucleotide sequence as shown in SEQ ID NO: 1 or 3, those skilled in the art may change remaining nucleotide sequence of inactive sites, so that the nucleotide sequence of an obtained transaminase has at least more than 80% identity to the nucleotide sequence as shown in SEQ ID NO: 1 or 3, and the transaminase obtained in this way has the same transaminase activity as that of a transaminase having nucleotide sequence as shown in SEQ ID NO: 1 or 3.

The nucleotide sequence capable of hybridizing with the nucleotide sequence as shown in SEQ ID NO: 1 or 3 under highly stringent conditions and encoding the omega-transaminase having the high stereoselective R-configuration catalytic activity is not the nucleotide sequence as shown in SEQ ID NO: 5 or 6. Similarly, a nucleotide sequence that can be hybridized with the nucleotide sequence as shown in SEQ ID NO:1 or 3 under highly stringent conditions and encodes the omega-transaminase having the high stereoselective R-configuration catalytic activity is screened based on the nucleotide sequence as shown in SEQ ID NO: 1 or 3, and a variant sequence of the nucleotide sequence as shown in SEQ ID NO: 1 or 3, which is obtained in this way, have the same transaminase activity as that of the transaminase having the nucleotide sequence as shown in SEQ ID NO: 1 or 3.

The stereoselectivity means that when two stereoisomers A and B are generated in a reaction, the yield of A is more than that of B, and the high stereoselectivity refers to the content of one of the stereoisomers being at least about 1.1 times that of the other, e.g. at least about 1.2 times, at least about 1.3 time, at least about 1.4 times, at least about 1.5 times, at least about 2 times, at least about 3 times, at least about 4 times, at least about 5 times, at least about 10 times, at least about 15 times, at least about 20 times, at least about 30 times, at least about 40 times, at least about 50 times, at least about 70 times, at least about 90 times, at least about 100 times or higher.

An exemplary highly stringent condition may be that the hybridization is performed at 65° C. by using 6×SSC and a 0.5% SDS solution, and membrane washing is performed by 2×SSC, 0.1% SDS and 1×SSC, and 0.1% SDS once respectively.

The term "identity" used in the present invention has a meaning generally known in the art. Those skilled in the art are also familiar with rules and standards for measuring the identity between different sequences. Sequences limited by the present invention with identities of different degrees also need to have the activity of the omega-transaminase with the high stereoselectivity R-configuration catalytic activity at the same time. Those skilled in the art generally know methods and means for screening the variant sequences by using the activity of the omega-transaminase with the high stereoselective R-configuration catalytic activity, and may be taught by the content disclosed by the application to acquire such variant sequences easily.

It is known by those skilled in the art that a qualifier used for limiting the amino acid sequences or polynucleotides is "include", but it does not mean that other sequences unrelated to functions of the amino acid sequences or polynucleotides may be added randomly to two ends of the amino acid sequences or polynucleotides. It is known by those skilled in the art that it is necessary to add proper restriction sites of restriction endonuclease, or additional initiator codons or stop codons and so on to both ends of the polynucleotides so as to meet requirements of a recombination operation. Therefore, these situations cannot be truly covered if the sequences are limited by closed expression.

It is generally known by those skilled in the art that one or more codons in the nucleotide sequences may be replaced equivalently without changing the encoded amino acids. For example, the leucine Leu encoded by CTT is replaced by CTA, CTC or CTG, and the number of replaced codons may be one or more, e.g. 1, 2, 3, 4, 5, 6, 8, 9, 10, 15, 20, 30, 40 or 50, and a codon usage table is generally known in the art.

A recombinant vector is provided according to another aspect of the present invention. Any foregoing nucleotide is effectively connected in the recombinant vector. The recombinant vector of the present invention includes, but is not limited to a recombinant expression vector, and may also include a recombinant cloning vector. The recombinant vector may be a prokaryotic expression vector or a eukaryotic expression vector. In an embodiment of the present invention, the recombinant vector is a recombinant prokaryotic expression vector that can induce expression, e.g. a pET series vector that induces gene expression by IPTG, such as a pET22b vector. In the present invention, recombinant vectors having the nucleotide sequence as shown in SEQ ID NO: 1 and SEQ ID NO: 3 are pET22b-CM32 and pET22b-CM33, wherein the "effectively connected" refers to such a connection method that a polynucleotide is placed at a proper location of the vector so that the polynucleotide is copied, transcribed and/or translated correctly and smoothly.

A host cell is provided according to another aspect of the present invention. Any foregoing recombinant vector is transformed or transfected into the host cell. The host cell of the present invention includes a prokaryotic host cell and a eukaryotic host cell. In an embodiment of the present invention, the host cell is a prokaryotic host cell, such as *Escherichia Coli*, preferably, DH5α (DE3).

A method for synthesizing a chiral amine is provided according to another aspect of the present invention. The method includes the following steps: making a ketone compound, any omega-transaminase of R-configuration or the modified compound, functional equivalent, functional fragment or variant thereof, pyridoxal phosphate, and an amino donor to react in a reaction system so as to obtain the chiral amine. The method for synthesizing a chiral amine according to the present invention only needs to utilize the transaminase of the present invention and make appropriate adjustment to parameters including the components, proportions, use amounts, pH values, temperature and reaction time and so on of reaction raw materials of the reaction system based on a conventional method for preparing a chiral compound through a reaction catalyzed by a biological enzyme in the art.

In a preferred embodiment of the present invention, the ketone compound is

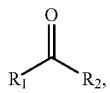

where $R_1$ and $R_2$ are independently $C_1$ to $C_8$ alkyl, $C_5$ to $C_{10}$ cycloalkyl, $C_5$ to $C_{10}$ aryl or $C_5$ to $C_{10}$ heteroaryl; or $R_1$ and $R_2$ form a $C_5$ to $C_{10}$ heterocyclic radical, a $C_5$ to $C_{10}$ carbocyclic radical or $C_5$ to $C_{10}$ heteroaryl with a carbon on a carbonyl group; heteroatoms in the $C_5$ to $C_{10}$ heterocyclic radical and $C_5$ to $C_{10}$ heteroaryl are independently selected from at least one of nitrogen, oxygen and sulfur; the aryl in the $C_5$ to $C_{10}$ aryl, the heteroaryl in the $C_5$ to $C_{10}$ heteroaryl, the carbocyclic radical in the $C_5$ to $C_{10}$ carbocyclic radical or the heterocyclic radical in the $C_5$ to $C_{10}$ heterocyclic radical is independently unsubstituted or is substituted by at least one radical of halogen, alkoxy or alkyl; preferably, the ketone compound

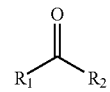

is selected from

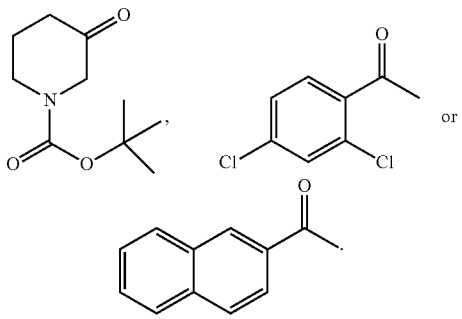

The ketone compound is a commercial raw material or a raw material that can be prepared easily and is cheap, and can therefore satisfy demands of mass production.

In another preferred embodiment of the present invention, the reaction system further includes a dissolution promoter, and the dissolution promoter is dimethyl sulfoxide or polyethylene glycol, and the polyethylene glycol is preferably PEG-400. The dissolution promoter can better dissolve the raw materials above so that the reaction can be carried out, and PEG-400 has the best dissolution promoting effect.

In another preferred embodiment of the present invention, the C1 to C8 alkyl is C1 to C8 linear alkyl, the C5 to C10 heteroaryl is a pyridine group, the alkoxy is C1 to C6 alkoxy, the heterocyclic radical in the C5 to C10 heterocyclic radical is piperidine, a substituent on the aryl in the C5 to C10 aryl, the heteroaryl in the C5 to C10 heteroaryl, the carbocyclic radical in the C5 to C10 carbocyclic radical or the heterocyclic radical in the C5 to C10 heterocyclic radical is independently C1 to C6 linear alkyl or C1 to C6 alkoxy, and the amino donor is isopropylamine or D-alanine. The raw materials above are commercial raw materials or raw materials that can be prepared easily and are cheap, and can therefore satisfy demands of large-scaled production.

In a preferred embodiment of the present invention, the reaction system contains a buffer solution for maintaining the pH value of the reaction system in a range of 7.0 to 9.5, and/or wherein the ratio of the use amount of the ketone compound to that of the dissolution promoter is 1 g/1 mL to 15 mL; and/or wherein the ratio of the use amount of the ketone compound to that of the buffer solution is 1 g/15 mL to 50 mL, and/or wherein the ratio of the use amount of the ketone compound to that of pyridoxal phosphate is 1 g/0.01 g to 0.1 g, and/or wherein the ratio of the use amount of the ketone compound to that of the amino donor is 1 eq/1 eq to 5 eq, and/or wherein the ratio of the use amount of the ketone compound to that of the omega-transaminase of R-configuration is 1 g/0.2 g to 10 g; and/or wherein the temperature of the reaction system is 20° C. to 45° C. and the reaction time is 12 h to 48 h, and/or wherein the buffer solution is a phosphate buffer solution or a triethanolamine having a pH value of pH=9.3 to 9.5.

In another preferred embodiment of the present invention, the method further includes a step that the reaction system is regulated to pH≥10 by an alkaline, and a product chiral amine in an aqueous phase is extracted by an organic solvent. Preferably, the alkaline is sodium hydroxide or potassium hydroxide, and the organic solvent is ethyl acetate, methyl tert-butyl ether or 2-methyltetrahydrofuran.

An R-configuration chiral amine is provided in another typical embodiment of the present invention. The R-configuration chiral amine is synthesized by using any method above. The R-configuration chiral amine prepared by the transaminase of the present invention has a high chiral purity which may be as high as more than 98%.

The beneficial effect of the present invention will be described below in combination with specific embodiments.

The methods are conventional methods unless otherwise specified in the following embodiments and the used experimental materials may be obtained easily from commercial corporations unless otherwise specified.

Embodiment 1: Preparation of Transaminase AH-TACM33 Derived from *Aspergillus terreus* and *Hyphomonas neptunium*

Specific steps of a preparation method of a transaminase AH-TACM33 of the present invention are as follows:

(1) Template Construction

Sangon Biotech (Shanghai) Co., Ltd. is entrusted to carry out whole gene synthesis of transaminase genes taAT (*Aspergillus terreus*) (the nucleotide sequence is the gene sequence as shown in SEQ ID NO: 5 in the sequencing list, and the amino acid sequence is as shown in SEQ ID NO: 23) and taHN (*Hyphomonas neptunium*) (the nucleotide sequence is the gene sequence as shown in SEQ ID NO: 6 in the sequencing list, and the amino acid sequences as shown in SEQ ID NO: 24) derived from *Aspergillus terreus* and *Hyphomonas neptunium*. The synthesized genes taAT and taHN are connected to a vector pUC57 respectively to obtain recombinant plasmids pUC57-taAT and pUC57-taHN, then the recombinant plasmids pUC57-taAT and pUC57-taHN are subjected to enzyme digestion simultaneously by using restriction endonuclease Nde I and Xho I, and purified recovered fragments taAT and taHN are obtained through gel recovery and used as templates of PCR in the next step.

(2) Primer Design

Specific primers designed according to the transaminase gene derived from *Aspergillus terreus* are as follows:

```
taAT A:
                                        (SEQ ID NO: 7)
5'-CCGCTCGAGGTTACGCTCGTTGTAGTCAATTTC-3' taAT S:
                                        (SEQ ID NO: 8)
5'-GGAATTCCATATGGCGTCTATGGACAAAG-3'
```

Specific primers designed according to the transaminase gene derived from *Hyphomonas neptunium* are as follows:

```
taHN A:
                                        (SEQ ID NO: 9)
5'-CCGCTCGAGCGGTGCATAGGTTACCGGTTC-3' taHN S:
                                        (SEQ ID NO: 10)
5'-GGAATTCCATATGCTGACCTTCCAAAAAGTACTGAC-3'
```

In the meanwhile, 6 pairs of primers are designed according to different sites, which are respectively as follows:

```
CM31A:
                                        (SEQ ID NO: 11)
5'-GAACTTCAGACCGCGGGTGACAATCAG-3'

CM31S:
                                        (SEQ ID NO: 12)
5'-CACCCGCGGTCTGAAGTTCCTGC-3'

CM32A:
                                        (SEQ ID NO: 13)
5'-CGGCGGAACACGACGAACGGTACG-3'

CM32S:
                                        (SEQ ID NO: 14)
5'-TTCGTCGTACTCCGCCGGGCGCAC-3'

CM33A:
                                        (SEQ ID NO: 15)
5'-TAGCCTGCGCCCTCGGTCAGGTGAG-3'

CM33S:
                                        (SEQ ID NO: 16)
5'-GACCGAGGGCGCAGGCTACAATATC-3'

CM34A:
                                        (SEQ ID NO: 17)
5'-CCCTTCAGACCACGCGTAACGATGATC-3'

CM34S:
                                        (SEQ ID NO: 18)
5'-TTACGCGTGGTCTGAAGGGTGTGCGTG-3'

CM35A:
                                        (SEQ ID NO: 19)
5'-CCAGGCGGAGTACGACGTACAGTACGAG-3'

CM35S:
                                        (SEQ ID NO: 20)
5'-TACGTCGTGTTCCGCCTGGCGCAATC-3'

CM36A:
                                        (SEQ ID NO: 21)
5'-GCCGCTGCCTTCCGTCGCGTTACC-3'

CM36S:
                                        (SEQ ID NO: 22)
5'-GACGGAAGGCAGCGGCTTCAACATC-3'
```

(3) Acquisition of a New Transaminase

The specific primer taAT S (a forward primer) designed on the transaminase gene derived from *Aspergillus terreus* is combined with any reverse primer in 3 reverse primers (CM31A, CM32A, CM33A) among the above 6 pairs of primers to amplify a fragment of the transaminase gene derived from *Aspergillus terreus*, or taHN A (a reverse primer) is combined with any one of 3 forward primers (CM36S, CM35S and CM34S) among the 6 pairs of primers to amplify a fragment of the transaminase gene derived from *Hyphomonas neptunium*. Subsequently, the two fragments of different origins, which are obtained from the amplification, are integrated so as to obtain a transformed transaminase gene.

Similarly, the specific primer taAT A (a reverse primer) designed on the transaminase gene derived from *Aspergillus terreus* is combined with any forward primer in 3 forward primers (CM33S, CM32S, CM31S) among the 6 pairs of primers to amplify a fragment of the transaminase gene derived from *Aspergillus terreus*, or taHN S (a forward primer) is combined with any one of 3 reverse primers (CM34A, CM35A and CM36A) among the 6 pairs of primers to amplify a fragment of the transaminase gene derived from *Hyphomonas neptunium*. Subsequently, the two fragments of different origins, which are obtained from the amplification, are integrated so as to obtain a transformed transaminase gene.

Specific transformation steps are expounded by taking a transaminase obtained by integrating the fragment acquired by amplifying the forward primer taAT S and the reverse primer CM33A and the fragment obtained by amplifying the reverse primer taHN A and the forward primer CM33S, and a transaminase obtained by integrating the fragment acquired by amplifying the forward primer taAT S and the reverse primer CM32A and the fragment acquired by amplifying the reverse primer taHN A and the forward primer CM32S as examples.

Steps for obtaining the transaminase AH-TACM33 are as follows:

Step 1: Acquisition of fragment A: the recovered fragment taAT is used as a PCR template, taAT S and CM33A are used as primers to perform PCR amplification and a product is recovered by gel extraction and purification to acquire a fragment A.

Step 2: Acquisition of fragment B: the recovered fragment taHN is used as a PCR template, taHN A and CM33S are used as primers to perform PCR amplification and a product is recovered by gel extraction and purification to acquire a fragment B.

Step 3: Acquisition of fragment CM33: the acquired fragment A and fragment B are used as templates and primers for each other, PCR amplification is performed for 5 cycles, then the primers taAT S and taHN A are added into the PCR system directly, overlapped PCR amplification is performed, and a product is recovered by gel extraction and purification to acquire a fragment CM33.

PCR system: fragment A 1 μL, fragment B 1 μL, PCR MIX 5 μL, ddH$_2$O 4.5 μl.

PCR procedure: 95° C. 3 min; (95° C. 30 s, 57° C. 30 s, 72° C. 90 s, 5 cycles); 72° C. 1 min.

0.2 μL of the primer taAT S and 0.2 μL of the primer taHN A are added into the system respectively.

PCR procedure: 95° C. 3 min; (95° C. 30 s, 57° C. 30 s, 72° C. 90 s, 30 cycles); 72° C. 10 min.

Step 4: Acquisition of recombinant plasmid pET22b-CM33: the fragments CM33 and pET-22b (+) are subjected to enzyme digestion simultaneously by using Nde I and Xho 1, ligation is performed by using a T4 DNA ligase, and a ligation product is transformed into a competent cell of an DH5α strain of *Escherichia coli*, resuscitated by a shaker, and then coated in an LB culture dish containing ampicillin having a final concentration of 50 μg/ml, and cultured overnight in an incubator at 37° C. A single colony on the culture dish is selected and inoculated in an LB liquid culture medium containing ampicillin having a final concentration of 50 μg/ml, and subjected to shake culture at 180 r/min and 37° C. overnight. A plasmid is extracted, subjected to PCR and identified by enzyme digestion, and an identification result of the enzyme digestion is as shown in FIG. 3.

FIG. 3 shows an identification diagram of the plasmid pET22b-CM33 having subjected to double digestion of the enzyme Nde I and the enzyme Xho I, wherein 1 represents an empty vector pET22b; 2 represents markers of the sizes of DNA molecules (10000 bp, 8000 bp, 6000 bp, 5000 bp, 4000 bp, 3500 bp, 3000 bp, 2500 bp, 2000 bp, 1500 bp, 1000 bp, 750 bp, 500 bp, 250 bp respectively from top to bottom) and 3 represents pET22b-CM33-DH5α. It may be seen from FIG. 3 that a relatively weak band having a fragment size of about 1000 bp after the enzyme digestion is a target fragment (a plasmid band having the target fragment removed is relatively strong), thus it may be determined that the insertion direction and size of an insertion sequence of the recombinant plasmid pET22b-CM33 are correct.

Step 5: Acquisition of BL21/pET22b-CM33: the obtained recombinant plasmid pET22b-CM33 is directly transformed into *Escherichia coli* BL21 (DE3), resuscitated by a shaker, and then coated in an LB culture dish containing ampicillin having a final concentration of 50 μg/ml, and cultured at 37° C. overnight; a single colony in the culture dish is selected and inoculated in 5 ml of an LB liquid culture medium containing ampicillin having a final concentration of 50 μg/ml, and cultured at 180 r/min and 37° C. overnight; bacterial liquid is sent to Sangon Biotech (Shanghai) Co., Ltd. to be sequenced, and after being verified correctly through gene sequencing, the plasmid is named BL21/pET22b-CM33.

The sequencing result is shown in FIG. 4 and it may be seen from FIG. 4 that the gene sequence carried by the BL21/pET22b-CM33 plasmid in the sequencing result is completely as expected and there is no mutated base. After being identified correctly by the sequencing, the recombinant plasmid is a target plasmid sequence.

Step 6: Preparation of transaminase AH-TACM33: a bacterial liquid of the BL21/pET22b-CM33 is transplanted in an LB liquid culture medium containing ampicillin having a final concentration of 50 μg/ml, subjected to shake culture at 180 r/min and 37° C., and when the OD600 value is 0.6 to 0.8, IPTG is added until the final concentration is 0.2 mM, and the culture solution is transposed at 25° C. to induce expression; after the induction is performed for 16 h, the bacterial liquid is taken out and centrifuged at 12000 r/min for 10 min, and thalli are collected; after cells are disrupted, the thalli are centrifuged at 4° C. and 12000 r/min for 20 min to obtain a supernatant which is a prepared transaminase AH-TACM33 having an amino acid sequence as shown in SEQ ID NO: 4 and a corresponding nucleotide sequence as shown in SEQ ID NO: 3.

Embodiment 2: Activity Experiment 1 of Transaminase AH-TACM33

1g of a major raw material (N-Boc-3-piperidone, CAS: 98977-36-7) and 1 mL of dimethyl sulfoxide are added into a reaction flask. After the raw materials are dispersed, 50 mL of a triethanolamine buffer solution having a concentration of 0.2mol/L and a pH value regulated to 9.3 to 9.5 by concentrated hydrochloric acid in an ice bath, 0.765g of isopropylamine, 0.01g of pyridoxal phosphate, and 0.01g of the transaminase AH-TACM33 are added, and stirred for 12h at a constant temperature of 30° C., wherein the pH value of the system is 9.5. The pH value of the system is regulated to above 10 by 2N NaOH, extraction is performed twice by ethyl acetate, and an organic phase is dried, filtered and concentrated to obtain a crude product (English name: (R)-1-N-Boc-3-aminopiperidine, CAS: 188111-79-7). It is detected by Gas Chromatography (GC) that the conversion rate is 90% and the e.e value is 100%.

Nuclear Magnetic Resonance (NMR) data of the obtained product is as follows: 1H-NMR (300 MHz, CDCl3) δ 4.00-3.78 (m, 2H), 3.80 (m, 2H), 3.60 (m, 1H), 1.90 (m, 1H). 1.70 (m, 1H), 1.60-1.40 (m, 12H), 1.30 (m, 1H) ppm.

Embodiment 3: Activity Experiment 2 of Transaminase AH-TACM33

0.1g of a major raw material (2,4-dichloroacetophenone, CAS:2234-16-4) and 1.5 mL of polyethylene glycol PEG-400 are added into a reaction flask. After the raw materials are dispersed, 23.5 mL of a phosphate buffer solution (pH8.0), 0.031g of isopropylamine, 0.0075g of pyridoxal phosphate, and 0.02g of the transaminase AH-TACM33 are added, and stirred for 20h at a constant temperature of 45° C., wherein the pH value of the system is 8.0. The pH value of the system is regulated to above 10 by 2N NaOH, extraction is performed twice by ethyl acetate, and an organic phase is dried, filtered and concentrated to obtain a crude product ([(R)-(+)-1-(2,4-dichlorophenyl) ethyl]amine, CAS: 133773-29-2). It is detected by GC that the conversion rate is 82% and the e.e value is 100%.

NMR data of the obtained product is as follows: 1H NMR (400 MHz, DMSO D6): δ=7.67 (d 1H), 7.60 (d, 1H), 7.47 (dd, 1H), 7.34 (dd, 4H), 7.23-7.12 (m, 6H), 4.84 (s, 1H), 4.47 (quartet, 1H), 1.31 (d, 3H).

Embodiment 4: Preparation of Transaminase AH-TACM32 Derived from *Aspergillus terreus* and *Hyphomonas neptunium*

Specific steps of a preparation method of a transaminase AH-TACM32 of the present invention are as follows:

(1) Template Construction

Recombinant plasmids pUC57-taAT and pUC57-taHN are obtained according to the method of Embodiment 1. The recombinant plasmids pUC57-taAT and pUC57-taHN are subjected to enzyme digestion simultaneously by using restriction endonuclease Nde I and Xho I, and purified recovered fragments taAT and taHN are obtained through gel recovery and used as templates of PCR in the next step.

(2) Primer Design

Primer design is the same as Embodiment 1.

(3) Acquisition of a New Transaminase

Step 1: Acquisition of fragment E: the recovered fragment taAT is used as a PCR template, taAT S and CM32A are used as primers to perform PCR amplification and a product is recovered by gel extraction and purification to acquire a fragment E.

Step 2: Acquisition of fragment F: the recovered fragment taHN is used as a PCR template, taHN A and CM32S are used as primers to perform PCR amplification and a product is recovered by gel extraction and purification to acquire a fragment F.

Step 3: Acquisition of fragment CM32: the acquired fragment E and fragment F are used as templates and primers for each other, PCR amplification is performed for 5 cycles, then the primers taAT S and taHN A are added into the PCR system directly, overlapped PCR amplification is performed, and a product is recovered by gel extraction and purification to acquire a fragment CM32.

Step 4: Acquisition of recombinant plasmid pET22b-CM32: the fragments CM32 and pET-22b (+) are subjected to enzyme digestion simultaneously by using Nde I and Xho I, ligation is performed by using a T4 DNA ligase, and a ligation product is transformed into a competent cell of an DH5α strain of *Escherichia coli*, resuscitated by a shaker, and then coated in an LB culture dish containing ampicillin having a final concentration of 50 μg/ml, and cultured overnight in an incubator at 37° C. A single colony on the culture dish is selected and inoculated in an LB liquid culture medium containing ampicillin having a final concentration of 50 μg/ml, and subjected to shake culture at 180 r/min and 37° C. overnight. A plasmid is extracted, subjected to PCR and identified by enzyme digestion, and an identification result of the enzyme digestion is as shown in FIG. 5.

Figures 5, 6:
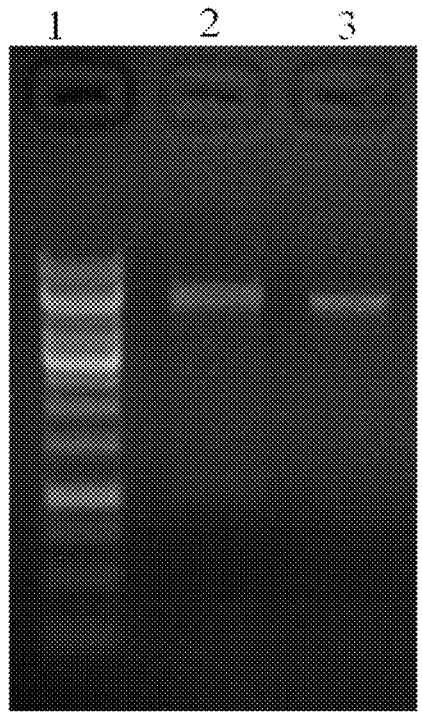
FIG. 5 shows an identification result of enzyme digestion in the fourth embodiment of the present invention.
FIG. 6 shows a sequencing result of a mutant gene having been subjected to a PCR in the fourth embodiment of the present invention.

FIG. 5 shows an identification diagram of the plasmid pET22b-CM32 having subjected to double digestion of the enzyme Nde I and the enzyme Xho I, wherein 1 represents markers of the sizes of DNA molecules (10000 bp, 8000 bp, 6000 bp, 5000 bp, 4000 bp, 3500 bp, 3000 bp, 2500 bp, 2000 bp, 1500 bp, 1000 bp, 750 bp, 500 bp, 250 bp from top to bottom), 2 represents pET22b-CM32-DH5α and 3 represents an empty vector pET22b.

It may be seen from FIG. 5 that a relatively weak band having a fragment size of about 1000 bp after the enzyme digestion is a target fragment (a plasmid band having the target fragment removed is relatively strong), thus it may be determined that the insertion direction and size of an insertion sequence of the recombinant plasmid pET22b-CM32 are correct, so as to obtain the recombinant plasmid pET22b-CM32.

Step 5: Acquisition of BL21/pET22b-CM32: the obtained recombinant plasmid pET22b-CM32 is directly transformed into *Escherichia coli* BL21 (DE3), resuscitated by a shaker, and then coated in an LB culture dish containing ampicillin having a final concentration of 50 μg/ml, and cultured at 37° C. overnight; a single colony in the culture dish is selected and inoculated in 5 ml of an LB liquid culture medium containing ampicillin having a final concentration of 50 μg/ml, and cultured at 180 r/min and 37° C. overnight; bacterial liquid is sent to Sangon Biotech (Shanghai) Co., Ltd. to be sequenced, and after being verified correctly through gene sequencing, the plasmid is named BL21/pET22b-CM32.

The sequencing result is shown in FIG. 6 and it may be seen from FIG. 6 that the gene sequence carried by the BL21/pET22b-CM32 plasmid in the sequencing result is completely as expected and there is no mutated base. After being identified correctly by the sequencing, the recombinant plasmid is a target plasmid sequence.

Step 6: Preparation of transaminase AH-TACM32: a bacterial liquid of the BL21/pET22b-CM32 is transplanted in an LB liquid culture medium containing ampicillin having a final concentration of 50 μg/ml, subjected to shake culture at 180 r/min and 37° C., and when the OD600 value is 0.6 to 0.8, IPTG is added until the final concentration is 0.2 mM, and the culture solution is transposed at 25° C. to induce expression; after the induction is performed for 16 h, the bacterial liquid is taken out and centrifuged at 12000 r/min for 10 min, and thalli are collected; after cells are disrupted, the thalli are centrifuged at 4° C. and 12000 r/min for 20 min to obtain a supernatant which is a prepared transaminase AH-TACM32 having an amino acid sequence as shown in SEQ ID NO: 2 and the corresponding nucleotide sequence as shown in SEQ ID NO: 1.

Embodiment 5: Activity Experiment of Transaminase AH-TACM32

0.1g of a major raw material (2-acetonaphthone, CAS: 93-08-3) and 1 mL of polyethylene glycol PEG-400 are added into a reaction flask. After the raw materials are dispersed, 24 mL of a phosphate buffer solution (pH7.0), 0.17g of isopropylamine, 0.01g of pyridoxal phosphate, and 0.004g of the transaminase AH-TACM32 are added, and stirred for 48h at a constant temperature of 20° C., wherein the pH value of the system is 7.0. The pH value of the system is regulated to above 10 by 2N NaOH, extraction is performed twice by ethyl acetate, and an organic phase is dried, filtered and concentrated to obtain a crude product ((R)-(+)-1-(2-naphthyl)ethylamine, CAS: 3906-16-9). It is detected by GC that the conversion rate is 20% and the e.e value is 100%.

NMR data of the obtained product is as follows: 1H NMR (400 MHz, CDCl3) δ 7.86-7.76 (m, 4H), 7.52-7.41 (m, 3H), 4.29 (q, J=6.4 Hz, 1H), 1.74 (br s, 2H), 1.48 (d, J=6.4 Hz, 3H).

The present invention further verifies the transaminase activity of the transaminase AH-TACM33 by using the major raw material (2-acetonaphthone, CAS: 93-08-3) and verifies the transaminase activity of the transaminase AH-TACM32 by using a major raw material (N-Boc-3-piperidone, CAS: 98977-36-7) and a major raw material (2,4-dichloroacetophenone, CAS:2234-16-4), specific method steps are the same as the embodiments above.

Embodiment 6

Based on the transaminase having an amino acid sequence as shown in SEQ ID NO: 2, the leucine at the 38th site of the transaminase is subjected to site-directed mutagenesis to be replaced with isoleucine, so as to obtain a transaminase having an sequence as shown in SEQ ID NO: 25.

An enzyme activity experiment is carried out to detect the transaminase, and detection steps are as follows:

a bacterial liquid of mutants is transplanted to 100 ml of an LB liquid culture medium containing ampicillin having a final concentration of 50 μg/ml, subjected to shake culture at 180 r/min and 37° C., and when the OD600 value is 0.6 to 0.8, IPTG is added until the final concentration is 0.2 mM, and the culture solution is transposed at 25° C. to induce expression. In the meanwhile, an IPTG inducer-free culture solution is set as a negative control. After the induction is performed for 16 h, the bacterial liquid is taken out and centrifuged at 12000 r/min for 5 min, and thalli are collected. 0.5 g of bacterial sludge is weighed and re-suspended in 2.5 mL of a phosphate buffer solution (pH8.0) and cells of the thalli are disrupted by an ultrasonic disrupter. Ultrasonic parameters include: probe diameter 6 mm, power 200 W, working time 2 s, and interval 6 s, totally 10 min. After the ultrasonic processing, centrifugation is performed at 12000 r/min for 20 min at 4° C. to obtain an ultrasonic supernatant and precipitate, and the supernatant is inputted in a reaction to verify transaminase activity.

0.1 g of a major raw material (acetophenone, CAS: 98-86-2) is added to a reaction flask, the raw material is dispersed in 13.5 mL of a phosphate buffer solution having a concentration of 0.1M (pH8.0), 0.356 g of D-alanine, 0.002 g of β-NAD+, 0.0192 g of lactic dehydrogenase, 0.006 g of glucose dehydrogenase, 0.432 g of glucose, 0.004 g of pyridoxal phosphate, and 2.5 mL of an omega-transaminase of R-configuration having a sequence encoded by SEQ ID NO: 25, the pH value of the system is 7.0, stirring is performed at a constant temperature of 30° C. for 16 h, the pH value of the system is regulated to above 10 by NaOH having a concentration of 2N, extraction is performed twice by ethyl acetate, and an organic phase is dried, filtered and concentrated to obtain a crude product (English name: (R)-1-phenethylamine, CAS: 3886-69-9). It is detected by GC that the conversion rate is 83% and the e.e value is 99.5%.

NMR data of the obtained product is as follows: 1H NMR (CDCl3, 400 MHz, 300K) δ (ppm): 7.36-7.29 (m, 4H), 7.26-7.19 (m, 1H), 4.11 (q, J=6.6 Hz, 1H), 1.53 (bs, 2H), 1.38 (d, J=6.6 Hz, 3H).

The result shows that the transaminase in the above embodiments of the present invention may achieve similar yields and enantiomer purity, thereby obtaining corresponding chiral amines of R-configuration.

It may be seen from the foregoing description that the embodiments of the present invention have achieved the following technical effect: a novel transaminase disclosed by the present invention catalyzes the transfer of an amino in an amino donor to prochiral ketones or aldehydes, thereby generating corresponding chiral amines of R-configuration. A target product having a high purity may be obtained by utilizing a synthesis method of the novel transaminase of the present invention, and the optical purity of the obtained product is stabilized at above 98%. The synthesis method, which is simple, applies easily available raw materials and has mild chemical reaction conditions, high yield and high enantiomer purity, and simple operations in the whole production process, is a feasible synthesis process with little pollution and provides a new approach and method for preparation of chiral amines.

The above are only preferred embodiments of the present invention, but are not used for limiting the present invention. For those skilled in the art, the present invention may have various modifications and changes. Any modifications, equivalent replacements, improvements and the like made within the spirit and principles of the present invention shall be included in the scope of protection of the present invention.

The invention claimed is:

1. A transaminase, wherein an amino sequence of the transaminase comprises the amino acid sequence of SEQ ID NO: 2 or an amino acid sequence acquired by substituting leucine at the 38th site of the amino acid sequence as shown in SEQ ID NO: 2 by isoleucine.

2. A method for synthesizing a chiral amine, wherein the method comprises the following steps: making a ketone compound, the transaminase according to claim 1, pyridoxal phosphate, and an amino donor to react in a reaction system so as to obtain the chiral amine of R configuration.

3. The method according to claim 2, wherein the ketone compound is

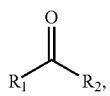

wherein $R_1$ and $R_2$ are independently $C_1$ to $C_8$ alkyl, $C_5$ to $C_{10}$ naphthenic base, $C_5$ to $C_{10}$ aryl or $C_5$ to $C_{10}$ heteroaryl; or $R_1$ and $R_2$ form a $C_5$ to $C_{10}$ heterocyclic radical, a $C_5$ to $C_{10}$ carbocyclic radical or $C_5$ to $C_{10}$ heteroaryl with a carbon on a carbonyl group; heteroatoms in the $C_5$ to $C_{10}$ heterocyclic radical and $C_5$ to $C_{10}$ heteroaryl are independently selected from at least one of nitrogen, oxygen and sulfur; the aryl in the $C_5$ to $C_{10}$ aryl, the heteroaryl in the $C_5$ to $C_{10}$ heteroaryl, the carbocyclic radical in the $C_5$ to $C_{10}$ carbocyclic radical or the heterocyclic radical in the $C_5$ to $C_{10}$ heterocyclic radical is independently unsubstituted or is substituted by at least one radical of halogen, alkoxy or alkyl.

4. The method according to claim 2, wherein the reaction system further includes a dissolution promoter, and the dissolution promoter is dimethyl sulfoxide or polyethylene glycol.

5. The method according to claim 3, wherein the C1 to C8 alkyl is C1 to C8 linear alkyl, the C5 to C10 heteroaryl is a pyridine group, the alkoxy is C1 to C6 alkoxy, the heterocyclic radical in the C5 to C10 heterocyclic radical is piperidine, a substituent on the aryl in the C5 to C10 aryl, the heteroaryl in the C5 to C10 heteroaryl, the carbocyclic radical in the C5 to C10 carbocyclic radical or the heterocyclic radical in the C5 to C10 heterocyclic radical is independently C1 to C6 linear alkyl or C1 to C6 alkoxy, and the amino donor is isopropylamine or D-alanine.

6. The method according to claim 3, wherein the reaction system further includes a dissolution promoter, and the dissolution promoter is dimethyl sulfoxide or polyethylene glycol.

7. A recombinant vector, wherein a nucleotide sequence encoding the transaminase according to claim 1 is connected in the recombinant vector.

8. The recombinant vector according to claim 7, wherein a sequence of the nucleotides includes the nucleotide sequence of SEQ ID NO: 1 or 3.

9. The recombinant vector according to claim 7, wherein the recombinant vector is pET22b-CM32 or pET22b-CM33.

10. A host cell transformed or transfected with the recombinant vector according to claim 7.

11. A host cell transformed or transfected with the recombinant vector according to claim 9.

12. The method according to claim 3, wherein the ketone compound

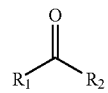

is selected from

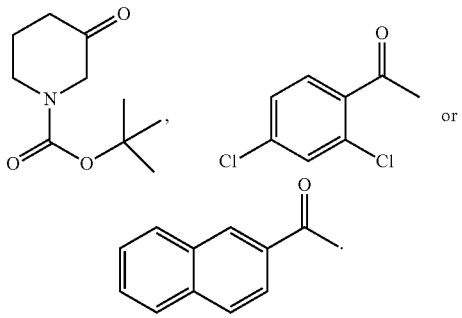

13. The method according to claim 4, wherein the polyethylene glycol is PEG-400.

14. The method according to claim 6, wherein the polyethylene glycol is PEG-400.

* * * * *